(12) United States Patent
Hansmann

(10) Patent No.: US 11,786,693 B2
(45) Date of Patent: Oct. 17, 2023

(54) DEVICE WITH AN INHALATION VALVE FOR A VENTILATION SYSTEM

(71) Applicant: Drägerwerk AG & Co. KGaA, Lübeck (DE)

(72) Inventor: Hans-Ullrich Hansmann, Barnitz (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 707 days.

(21) Appl. No.: 16/880,741

(22) Filed: May 21, 2020

(65) Prior Publication Data
US 2020/0368486 A1 Nov. 26, 2020

(30) Foreign Application Priority Data
May 24, 2019 (DE) .......................... 102019003643.3

(51) Int. Cl.
*A61M 16/00* (2006.01)
*A61M 16/20* (2006.01)

(52) U.S. Cl.
CPC ...... *A61M 16/204* (2014.02); *A61M 16/0057* (2013.01); *A61M 16/205* (2014.02);
(Continued)

(58) Field of Classification Search
CPC .. A61M 16/204; A61M 16/205; A61M 16/00; A61M 2205/3341; A61M 16/0057;
(Continued)

(56) References Cited

U.S. PATENT DOCUMENTS 3,339,545 A * 9/1967 Burchell ............... A61M 16/00
128/205.14
4,575,042 A * 3/1986 Grimland .......... A61M 16/0677
128/205.24
(Continued)

FOREIGN PATENT DOCUMENTS

DE 102016009836 A1 2/2018
EP 0669141 A2 * 2/1995 ............ A61M 16/00
(Continued)

OTHER PUBLICATIONS

Machine translation of written description and claims for JP5012889B2 (Year: 2012).*

*Primary Examiner* — Philip R Wiest
*Assistant Examiner* — Tyler A Raubenstraw
(74) *Attorney, Agent, or Firm* — McGlew and Tuttle, P.C.

(57) ABSTRACT

A device (1), for a ventilation system (100), includes an inhalation valve (10) with an inhalation opening (11) for flow (301) of breathing gas (300) into a pressure chamber (110) to provide breathing gas in the pressure chamber for ventilating a patient (200). A closing element (12) is arranged movably, to close the inhalation opening to flow in a closed position (320) and to at least partially release flow in an open position (310). A transmission device (13) is connected via a connection element (14) to the closing element, to hold the closing element in the closed position in a starting position of the transmission device, such that the inhalation valve is normally closed. A control pressure source (130) provides a control pressure (PS) in a control pressure chamber (15) for the transmission device to move the transmission device out of the starting position by the control pressure.

21 Claims, 10 Drawing Sheets

(52) U.S. Cl.
CPC ............... *A61M 2016/0027* (2013.01); *A61M 2205/0294* (2013.01); *A61M 2205/3341* (2013.01)

(58) Field of Classification Search
CPC .. A61M 16/20; A61M 16/206; A61M 16/207; A61M 2016/0027; A61M 2205/0294
See application file for complete search history.

(56) References Cited

U.S. PATENT DOCUMENTS

| | | | | |
|---|---|---|---|---|
| 5,484,270 | A * | 1/1996 | Adahan | A61M 16/204 417/415 |
| 5,598,838 | A * | 2/1997 | Servidio | A61M 16/204 128/204.26 |
| 5,839,436 | A | 11/1998 | Fangrow, Jr. et al. | |
| 5,896,857 | A * | 4/1999 | Hely | A62B 9/02 128/205.24 |
| 8,485,179 | B1 * | 7/2013 | Meyer | A61M 16/00 128/200.24 |
| 9,327,092 | B2 * | 5/2016 | Brambilla | A61M 16/0875 |
| 10,265,495 | B2 * | 4/2019 | Voss | A61M 16/208 |
| 10,406,314 | B2 * | 9/2019 | Dunkel | A61M 16/204 |
| 2004/0074494 | A1 * | 4/2004 | Frater | A61M 16/0072 128/204.23 |
| 2005/0039752 | A1 * | 2/2005 | Zaiser | A61M 16/20 128/205.24 |
| 2007/0215161 | A1 * | 9/2007 | Frater | A61M 16/065 128/206.24 |
| 2009/0241953 | A1 * | 10/2009 | Vandine | A61M 16/12 128/204.21 |
| 2011/0120473 | A1 * | 5/2011 | Piper | A61M 16/208 128/207.16 |
| 2011/0126837 | A1 * | 6/2011 | Winter | A61M 16/206 128/205.12 |
| 2015/0224269 | A1 * | 8/2015 | Alizoti | A61M 16/0003 128/205.23 |
| 2017/0216554 | A1 * | 8/2017 | Dunkel | A61M 16/204 |
| 2018/0110957 | A1 * | 4/2018 | Hansmann | A61M 16/20 |
| 2018/0133420 | A1 * | 5/2018 | Hansmann | A61M 16/201 |
| 2018/0243528 | A1 * | 8/2018 | Zapol | C01B 21/32 |

FOREIGN PATENT DOCUMENTS

| | | | | |
|---|---|---|---|---|
| GB | 2124909 | A * | 2/1984 | ............ A61M 16/00 |
| JP | 5012889 | B2 * | 8/2012 | .......... F04B 39/1093 |
| WO | WO-8702590 | A * | 5/1987 | ............ A61M 16/00 |
| WO | WO-2014043225 | A2 * | 3/2014 | ......... A61M 1/0031 |
| WO | WO-2016108129 | A1 * | 7/2016 | |
| WO | WO-2018074193 | A1 * | 4/2018 | .............. A61M 1/00 |

* cited by examiner

ID-DEVICE WITH AN INHALATION VALVE
FOR A VENTILATION SYSTEM

CROSS REFERENCE TO RELATED APPLICATIONS

This application claims the benefit of priority under 35 U.S.C. § 119 of German Application 10 2019 003 643.3, filed May 24, 2019, the entire contents of which are incorporated herein by reference.

TECHNICAL FIELD

The present invention pertains to a device with an inhalation valve for a ventilation system. The present invention further pertains to a ventilation system as well as to a process.

TECHNICAL BACKGROUND

Various types of exhalation valves and inhalation valves, which are used for ventilating patients, are known from the state of the art. Thus, exhalation valves are frequently used as so-called "normally closed" valves (also: N. C.) in order to set a so-called positive end-expiratory pressure (PEEP for short, Positive End Expiratory Pressure) during the ventilation of a patient during the exhalation phase. Inhalation valves may also be configured as so-called "normally open" valves (N. O.), which are open during inhalation and closed during exhalation.

Further, a control pressure, which actuates the inhalation valve, may be generated by a pump for regulating a flow of a breathing gas to the patient.

However, a drawback of conventional solutions is that the regulation of such inhalation valves may be associated with a greater technical effort.

Concretely, a permanently open state of the inhalation valve may develop in case of a defective actuation, e.g., during a failure of the pump. The flow of the breathing gas to the patient would thus take place unhindered unless further safety measures are taken.

SUMMARY

A basic object of the present invention is to at least partially reduce the above-described drawbacks. In particular, it is an object to provide an improved solution for controlling or regulating the ventilation close to the patient, during which a simple and stable pressure control is made possible. In addition, reducing the technical effort for a reliable operation of the inhalation valve may be an object.

The basic object is accomplished, in particular, by a device, preferably a valve device, with an inhalation valve (i.e., having an inhalation valve) for a ventilation system. Such an inhalation valve may be used for controlling the flow of a fluid during the inhalation process. The inhalation valve may have for this purpose an inhalation opening in order concretely to control the flow of a breathing gas into a pressure chamber and hereby to make the breathing gas in the pressure chamber usable for ventilating a patient. In other words, the inhalation opening of the inhalation valve is intended for the flow of the breathing gas into the pressure chamber in order to provide the breathing gas in the pressure chamber for ventilating the patient. In addition, a closing element of the inhalation valve may be provided, which closing element is arranged to close the inhalation opening for the flow in a closed position and to release it at least partially in an open position. The closed position can thus be used to prevent the flow, and the open position can correspondingly be used to make the flow possible. The actuation of a movement of the closing element from the closed position into the open position and/or vice versa can thus lead to a control of the flow. A permanent occurrence of the open position, e.g., in case of a defect of the control, cannot, however, possibly bring about a critical state.

The device according to the present invention may have, further, at least one of the following components, especially for preventing this critical state:

an (especially mechanical) transmission device of the inhalation valve, which transmission device is connected to the closing element via an (especially mechanical) connection element in order to hold the closing element in the closed position in a starting position of the transmission device, preferably such that the inhalation valve is provided as a normally closed inhalation valve for the ventilation system, and a control pressure source, such as a pump, for providing a control pressure in a control pressure chamber for the transmission device, in order to move the transmission device by the control pressure (especially by an increase in the control pressure) out of the starting position.

This may have the advantage that the closing element is held in the closed position according to the starting position of the transmission device in case of a failure of the control pressure source or of the control pressure. In other words, the inhalation valve can be closed "normally" (i.e., in the starting position when the control pressure ceases to be present).

In particular, provisions are made in this connection for the transmission device to be configured with the closing element for the force-transmitting coupling of the pressure chamber with the closing element, so that when the chamber pressure rises in the pressure chamber, the closing element is moved, outside of the starting position of the transmission device and especially against the control pressure, in the direction of the closed position. The advantage that the closed position can be brought about not only by the setting of the control pressure but already in the normal state, i.e., also when a control pressure fails to build up and the inhalation valve is closed during an increase in the chamber pressure can be achieved in this case as well. Even if the closing element is in a partially open state (in the open position), it may be moved possibly automatically into the closed position when the control pressure fails to build up or is reduced in order to automatically bring about at least a reduction of the flow of the breathing gas into the pressure chamber.

The starting position of the transmission device may be defined within the framework of the present invention as a state which the transmission device assumes without external energy supply, e.g., by a control pressure, especially additionally to the normally prevailing air pressure. The transmission device can be moved out of the starting position only when an additional force is applied, e.g., by increasing the control pressure, and this movement can be transmitted to the closing element via the connection element. The movement is configured here especially as a deflection, e.g., of the transmission device in the form of a diaphragm.

Provisions may be made for the transmission device to be configured to separate the control pressure chamber from the pressure chamber, preferably to separate it in a fluid-tight manner. The transmission device thus has an additional functionality, namely, especially the sealing of the control pressure chamber. The transmission device can thus have, in other words, a sealing function.

The advantage that an increasing chamber pressure automatically brings about a reduction of the flow of the breathing gas into the pressure chamber may possibly also be achieved by a device according to the present invention. This reduction of the flow may counteract a further increase in the chamber pressure and possibly also make possible a reduction of the chamber pressure. The operation of the inhalation valve is thus markedly simplified technically especially with respect to a regulation. The chamber pressure is especially specific to an airway pressure of the patient and/or corresponds to this.

Further, the movement of the closing element in the direction of the closed position may bring about a closing of the inhalation valve in order to reduce or to set the further flow of the breathing gas. The movement of the closing element in the direction of the open position can, by contrast, bring about the opening of the inhalation valve in order to increase the further flow of the breathing gas.

The present invention is also based, in particular, on the discovery that even though a conventional inhalation valve may also have the full functionality, an excessively high chamber pressure does nevertheless lead to an opening of the inhalation valve. Since the chamber pressure may correspond essentially to the airway pressure, this leads to an additional build-up of pressure in the airways. A controller must conventionally compensate this behavior permanently in a technically complicated manner on the basis of a return of the chamber pressure and/or of the airway pressure and/or of a control pressure. According to the present invention, the inhalation valve may therefore advantageously be configured such that a rising chamber pressure exerts an increasing, closing force on the inhalation valve. An increasing chamber pressure in the inhalation valve thus leads to an increasing closing of the inhalation valve, so that, in particular, an increasing pressure build-up of the chamber pressure can be reduced by preventing the further entry of the breathing gas, and the chamber pressure can preferably even be reduced. The chamber pressure is defined here as an equivalent to the control pressure for the inhalation valve. This has the further advantage that only a slow regulation is needed for flow pressure settings and only a control without returning the chamber pressure or the airway pressure is needed in the extreme case.

The control characteristic of the inhalation valve advantageously corresponds to that of a self-stabilizing pressure controller when a pressure increase in the chamber pressure in the pressure chamber leads to a movement of the closing element into the closed position and hence to a reduction of the entry of breathing gas into the pressure chamber. The reduction of the entry of breathing gas into the pressure chamber has, in turn, the advantage that the increase in the chamber pressure cannot be further intensified or even reduced by the breathing gas. The effort needed for regulating the inhalation valve can thus be markedly reduced. It is not necessary, for example, actively to counteract the regulation of the opening of the closing element (movement in the direction of the open position) by means of a control pressure. This takes place automatically based on the transmission device by the pressure increase in the pressure chamber.

In order to attain a higher dynamics of the inhalation valve with wide openings or high possible volume flows, it may, moreover, be useful actively to open wide the opening of the inhalation valve for expected high volume flows of the breathing gas. It may also be useful rapidly to close the inhalation valve by rapidly closing the inhalation valve when a target value for the chamber pressure is exceeded.

An exhalation valve used in connection with the inhalation valve may advantageously be configured such that an increasing chamber pressure leads to opening of the exhalation valve, so that the breathing gas escapes and the chamber pressure is thus reduced.

Further, it is possible to achieve within the framework of the present invention the further advantage that the operation of the inhalation valve is markedly simplified technically with a normally closed inhalation valve. It is advantageously also possible hereby to build a self-stabilizing pressure controller, in which, in particular, a rising chamber pressure leads to an increasing closing force acting on the inhalation valve, i.e., especially on the closing element thereof.

"Normally closed" may mean within the framework of the present invention that the valve is closed without external energy supply, e.g., by a control pressure, especially in addition to the normally prevailing air pressure. The inhalation valve is opened only when additional energy is applied, e.g., by increasing the control pressure for the inhalation valve.

Provisions may advantageously also be made for the transmission device further having:

a first area to which the chamber pressure from the pressure chamber is admitted in order to convert the increase in the chamber pressure into an increasing force for moving the closing element in the direction of the closed position, and a second area to which the control pressure from the control pressure chamber is admitted in order to convert an increase in the control pressure into an increasing force for moving the closing element in the direction of the open position, the first area and the second area being preferably arranged opposite each other in order to preferably convert the increase in the chamber pressure and in the control pressure into mechanical deflections of the transmission device in opposite directions.

In other words, a force from the pressure chamber, which force acts on the first area due to the pressure increase in the chamber pressure in the pressure chamber is converted into a mechanical deflection of the transmission device and thus—via the connection element—into the movement of the closing element into the closed position, and a force from the control pressure chamber, which force acts on the second area due to an increase in the control pressure, is converted, likewise possibly via the connection element, into the movement of the closing element into the open position, so that, in particular, the control pressure and the chamber pressure or an airway pressure interact competitively in the pressure chamber for providing opposite movements of the closing element. It is possible in this connection that the areas have different sizes in order to set the influence of the control pressure and of the chamber pressure differently. For example, the first area may be reduced for this purpose in relation to the second area by preventing the admission of the chamber pressure at the edge area of the transmission device (e.g., by a sealing and/or bonding and/or the like in this edge area).

Provisions may be made, for example, for the closing element to have a closing element area for closing the inhalation openings in the closed position, wherein the area ratio of the closing element area to the first area is in the range of 0.25 to 1, preferably in the range of 0.3 to 0.75, and preferably in the range of 0.5 to 0.6. The area ratio may be changed to adapt the control characteristic of the inhalation valve and/or to adapt the pressure ratios. For example, it can be guaranteed by selecting the ratio of the areas or surface areas that the chamber pressure exerts a stronger force on the first area than on the closing element, which causes the closing function of the inhalation valve (movement of the closing element into the closed position) to be accomplished with increasing closing force at a higher chamber pressure.

Provisions may be made in another possibility for the surface area of the second area to correspond to the surface area of the first area or to differ from them by a maximum of 10%. The control pressure and the chamber pressure can thus equally bring about the movement of the closing element. It may be possible, as an alternative, that the surface areas of the first and second areas differ from one another, preferably by more than 10%. This makes it possible, for example, to increase the influence of the control pressure on the movement of the closing element when the second area has a larger surface area than the first area. This makes possible the advantage that a less powerful and/or smaller control pressure source or pump can be used as well. This may also make it possible that the control pressure source or pump is fastened (directly) to the inhalation valve, preferably via a coupling element, so that, in particular, the device according to the present invention can be configured as an assembly unit. As an alternative, the control pressure source may also be connected to the control pressure chamber via a flexible tube (especially a pump tube).

Provisions may be made according to another advantage for the transmission device to be rigidly connected to the closing element via the connection element in order to move the closing element from the open position into the closed position preferably during an increase in the chamber pressure, especially during a pressure increase of an airway pressure (in the pressure chamber), which takes place on the basis of an exhalation process, and to maintain the closing element in the closed position in the closed state after the movement and/or in the starting position of the transmission device. In other words, the transmission device may be configured to convert the pressure increase of the chamber pressure into a force for moving the closing element in order to exert this force as an increasing closing force on the closing element, especially when the pressure increase of the chamber pressure is applied to the transmission device based on the exhaled air arriving from the patient in the pressure chamber.

It is advantageous, moreover, if the transmission device is configured in the form of a diaphragm, preferably in order to provide a movement of the closing element, especially the force-transmitting coupling, by a mechanical deflection of the diaphragm as a function of an increase in the control pressure and/or chamber pressure, the diaphragm preferably being connected to the closing element for transmitting the deflection to the closing element via the connection element. The use of a diaphragm may offer here a structurally simple and reliable possibility for the force-transmitting coupling of the pressure chamber with the closing element. The inhalation valve may thus be configured such that the rising chamber pressure exerts an increasing, closing force on the inhalation valve via the diaphragm Thus, the rising chamber pressure does not lead to an opening of the inhalation valve (i.e., of the inhalation opening through the closing element), which could lead to a further increase in the chamber pressure, but to a closing. The inhalation valve can thus compensate the chamber pressure independently, and the safety during the operation can be increased.

The diaphragm may, moreover, be so flexible in the relevant pressure range, e.g., in the range of 0 mbar to about 100 mbar in a ventilation system, that the center of the diaphragm surface can be displaced by an adjustment path, which is needed for opening the closing element of the inhalation valve, for example, by an adjustment path in the range of 0.1 mm to 3 mm (millimeters).

Furthermore, it is optionally possible within the framework of the present invention that the transmission device is configured to provide the functionality of a normally closed inhalation valve in the absence of control pressure (i.e., especially without the provision of the control pressure by the control pressure source or pump) in the starting position. The safety can be increased in this manner in a structurally simple manner and with little technical effort.

Provisions may advantageously be made in the present invention for the control pressure source to be configured as a pump and especially for the pump to be configured as a piezo pump, preferably in order to set the control pressure in the range of 0 mbar to 3 mbar and preferably at 0 mbar during an exhalation process of the patient.

Provisions may be made within the framework of the present invention for a control device being provided for an automatic control and/or regulation of the flow in order to determine the control pressure for moving the closing element in the direction of the open position and especially in order to provide the control pressure competitively with the chamber pressure in the pressure chamber, so that the movement of the closing element preferably depends on a ratio of the control pressure to the chamber pressure. This has the advantage that the device can be regulated safely and reliably for the ventilation.

The control device may further optionally be configured to carry out the regulation such that the inhalation valve opens especially wide at the beginning of an inhalation process, so that a desired pressure preset within the framework of the regulation and/or a desired pressure difference in the pressure chamber can be reached in a short time. A gas flow or gas flow-through or volume flow, which brings about the pressure difference during the flow-by, may also be referred to instead of a pressure difference.

Pressure increases due to coupling during inhalation can, for example, be compensated rapidly by the inhalation valve being closed briefly due to a pressure reduction in the control pressure chamber.

As an alternative to the regulation, an exclusive control by the control device may optionally be provided as well.

Especially for a periodic control, the inhalation valve may be actuated periodically with a control pressure. During a first phase, i.e., during inhalation, the inhalation valve may be actuated, for example, with a control pressure in the range of 10 mbar to 30 mbar, especially in the range of 15 mbar to 25 mbar. During a second phase, i.e., during exhalation, the inhalation valve may be actuated with a lower control pressure of 0 mbar, i.e., the inhalation valve is in its "normal state," i.e., in the closed state. The control may optionally be used without the use of the above-mentioned regulation. As an alternative, a superimposition to the regulation is possible.

Provisions may advantageously also be made for an auxiliary pressure chamber with a ventilation opening to be provided for passing on the breathing gas provided to the patient, in which case the auxiliary pressure chamber is connected to the pressure camber via a diaphragm opening in a fluid-communicating manner, and wherein at least one sensor array is preferably provided, in order to detect an actual pressure difference prevailing between the auxiliary pressure chamber and the pressure chamber, the control device being configured to determine a deviation of a desired pressure difference between the auxiliary pressure chamber and the pressure chamber and the detected actual pressure difference, in order to determine the control pressure as a function of the deviation. The regulation can thus be further improved.

The present invention also pertains to a ventilation system for ventilating a patient by means of a breathing gas, having at least:
- a gas source for providing the breathing gas,
- a device according to the present invention with an inhalation valve, wherein the inhalation valve is preferably configured as a normally closed inhalation valve, and
- an exhalation valve, which is preferably configured as a normally open exhalation valve.

The ventilation system according to the present invention thus offers the same advantages as the device according to the present invention, which was described in detail with reference to a device according to the present invention.

The normally open exhalation valve is advantageously characterized in that it is closed by an (additional) control pressure for the exhalation valve and is otherwise open in the absence of the (additional) control pressure.

The inhalation valve may optionally be used in a valve block for the ventilation system, especially for a ventilator or an anesthesia apparatus. The device according to the present invention may also be configured in this manner as an assembly unit. The ventilation system carries, for example, the breathing gas as a breathing gas mixture consisting of oxygen and nitrogen containing, for example, 79 vol. % of nitrogen and 21 vol. % of oxygen. Anesthetic chemical substances are added to the breathing gas mixture in the case of an anesthesia apparatus.

A valve block advantageously forms a housing around the inhalation valve and protects it from contamination and other environmental effects. Essential parts of the inhalation valve may optionally be carried by the valve block.

Provisions may be made in the present invention for the ventilation system to be configured such that a rising pressure of an exhaled air of the patient leads to an increase in the chamber pressure and consequently to the exertion of an increasing closing force on the closing element. The closing function of the inhalation valve can thus be intensified. The inhalation valve is closed especially during exhalation by the patient when no control pressure is present. Cough events during inhalation or even during exhalation can thus likewise lead to a closure of the inhalation valve or support the closing in addition to a regulation (closed loop) or control (open loop).

Further, it is possible that the inhalation valve has a closing edge, with which the closing element is brought into contact in the closed position of the inhalation valve.

A fluid, especially the breathing gas, which is sent through the inhalation valve into the pressure chamber, may have a pressure in the range of 30 mbar to 200 mbar and preferably in the range of 40 mbar to 150 mbar. An optimal mode of operation of the inhalation valve can be obtained for said pressure ratios and said area ratio, the pressure of the fluid being admitted being counteracted on opening the inhalation valve. The pressure of the fluid to be admitted is relevant for the self-stabilizing function of the inhalation valve to the extent that it likewise supports the closing.

Further, a ventilation opening of a valve block may be provided in order to introduce the exhaled air into the pressure chamber and to generate an airway pressure in the pressure chamber, the airway pressure preferably being able to be in the range of 30 mbar to 200 mbar. This airway pressure may further form (generate or influence) the chamber pressure.

The valve block may preferably have the exhalation valve, especially a normally open exhalation valve, preferably an exhalation valve with a piezo pump, which can be actuated within milliseconds and hence rapidly. In particular, provisions may be made for the exhalation valve to be closed during inhalation. The exhalation valve may optionally be used, in addition to the inhalation valve, to regulate a pressure difference by an actual pressure difference prevailing between an auxiliary pressure chamber or the auxiliary pressure chamber and the pressure chamber being detected, especially with the use of a diaphragm, which is preferably arranged between the auxiliary pressure chamber and the pressure chamber.

A control device may have a processing unit, such as a microprocessor and/or a processor, in order to carry out the control and/or regulation. The processing unit may process for this purpose, for example, program commands of a control and/or regulation program.

The present invention also pertains to a process for operating an inhalation valve of a ventilation system, in which the following steps are carried out:
- initiation, especially by a gas source, by a flow of a breathing gas through an inhalation opening of the inhalation valve into a pressure chamber, in order to provide the breathing gas in the pressure chamber for ventilating a patient.
- provision of a closing element of the inhalation valve, which is arranged movably, in order to close the inhalation opening for the flow in a closed position and to at least partially release it in an open position,
- provision of an especially mechanical transmission device of the inhalation valve, which is connected to the closing element via an especially mechanical connection element, in order to hold the closing element in a starting position of the transmission device in the closed position, preferably such that the inhalation valve is provided as a normally closed inhalation valve for the ventilation system, and
- provision of a control pressure source, preferably a pump, for providing a control pressure in a control pressure chamber for the transmission device in order to move the transmission device by the control pressure, especially by an increase in the control pressure, from the starting position, wherein the transmission device is configured for the force-transmitting coupling of the pressure chamber with the closing element, so that the closing element is moved in the direction of the closed position outside the starting position of the transmission device and especially against the control pressure when a chamber pressure rises in the pressure chamber.

The process according to the present invention thus offers the same advantages as those that were described in detail with reference to a device according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
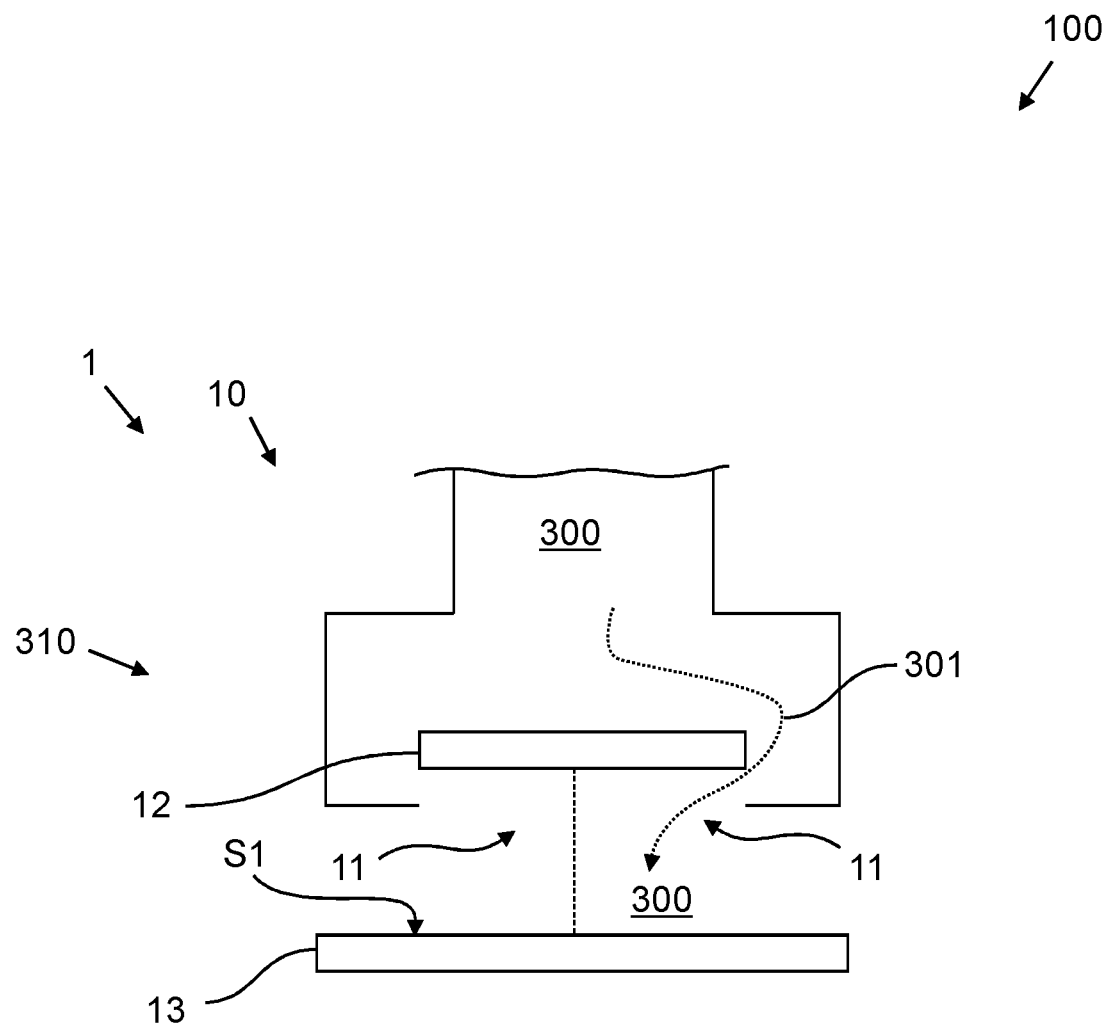
FIG. 1 is a schematic view of parts of a device according to the present invention in an open position.

Referring to the drawings, elements having the same function and mode of operation are always provided with the same reference numbers.

Figure 2:
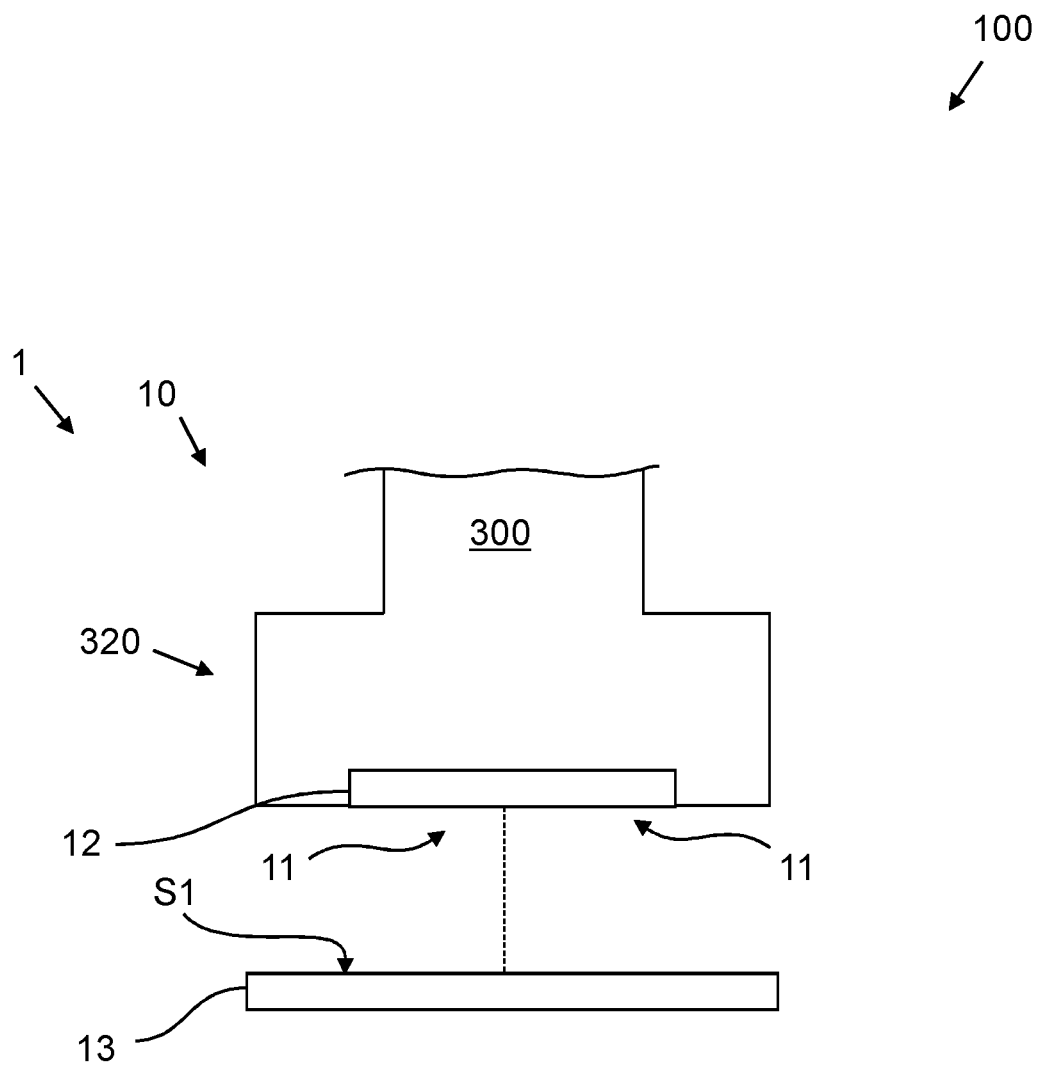
FIG. 2 is a schematic view of parts of a device according to the present invention in a closed position.
Figure 3:
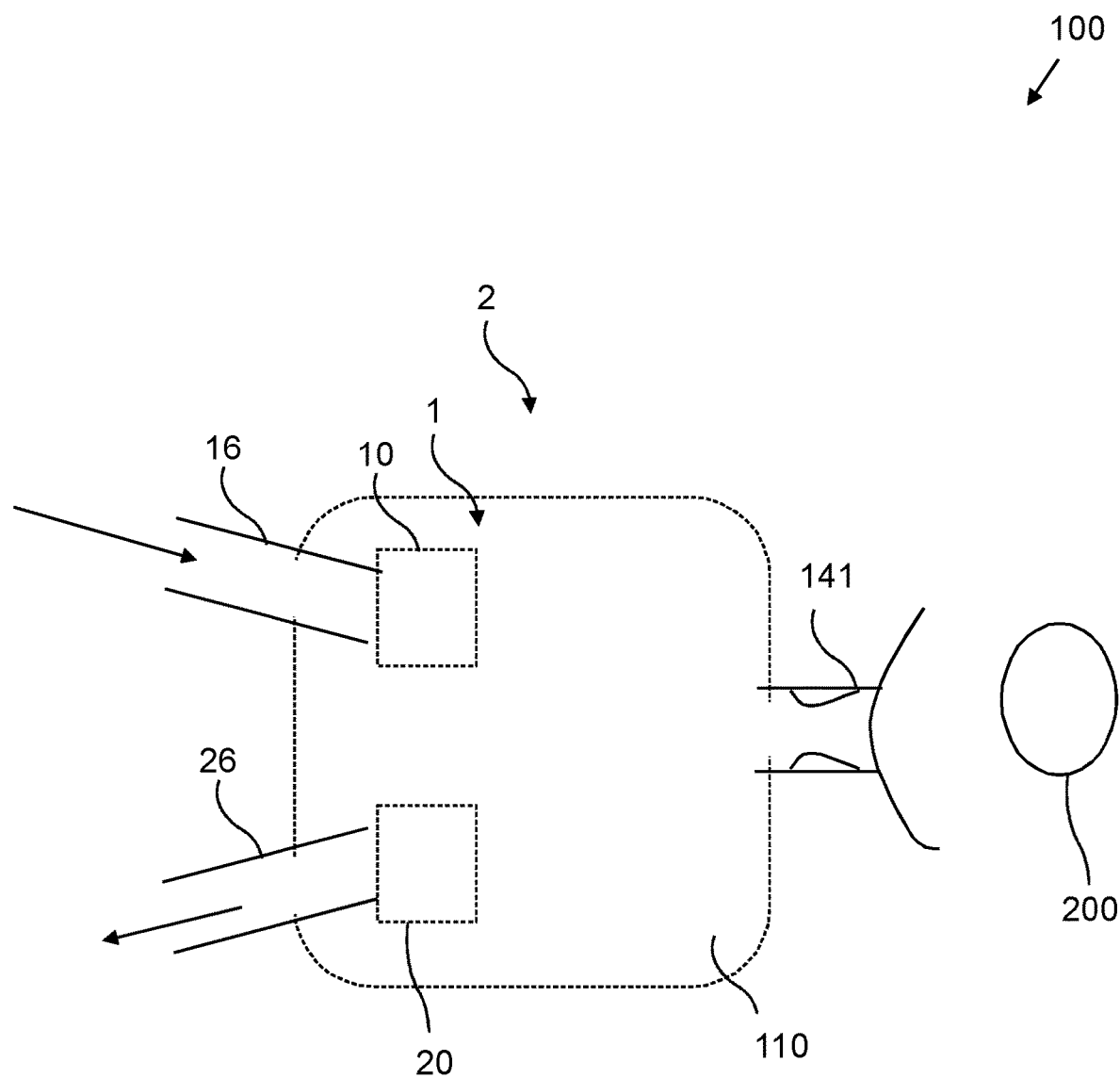
FIG. 3 is a schematic view of parts of a ventilation system according to the present invention.

FIGS. 1 through 3 show each parts of a device 1 according to the present invention. The device 1 comprises an inhalation valve 10 for a ventilation system 100. An inhalation opening 11 of the inhalation valve 10 is provided for a flow 301 of a breathing gas 300 into a pressure chamber 110 in order to provide the breathing gas 300 in the pressure chamber 110 for ventilating a patient 200. In addition, a closing element 12 of the inhalation valve 10 is arranged movably in order to close the inhalation opening 11 for the flow 301 in a closed position 320 and to at least partially release it in an open position 310. The open position 310 is visualized schematically in FIG. 1 and the closed position 320 is visualized schematically in FIG. 2.

Figure 4:
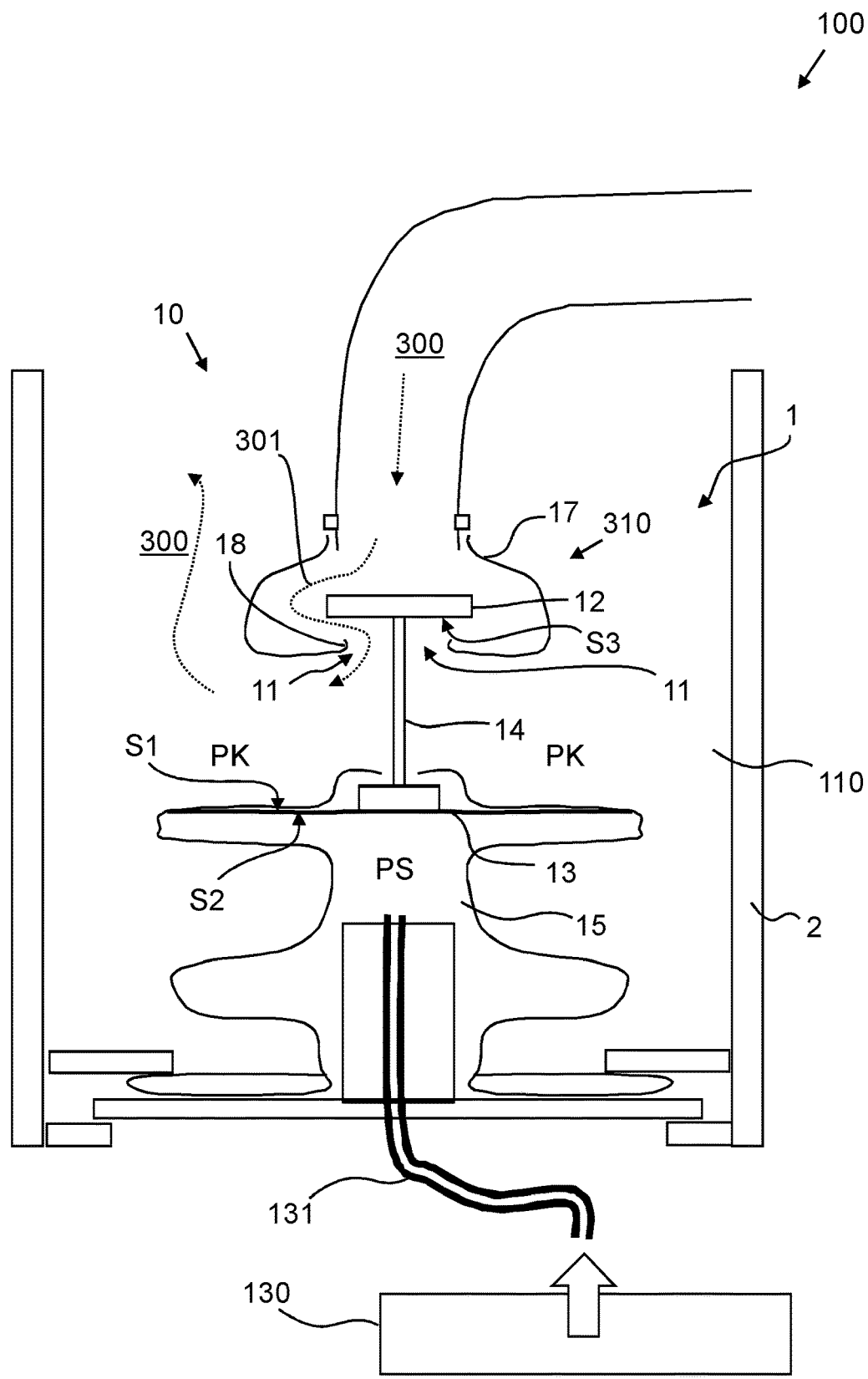
FIG. 4 is a schematic view of parts of a device according to the present invention.
Figure 6:
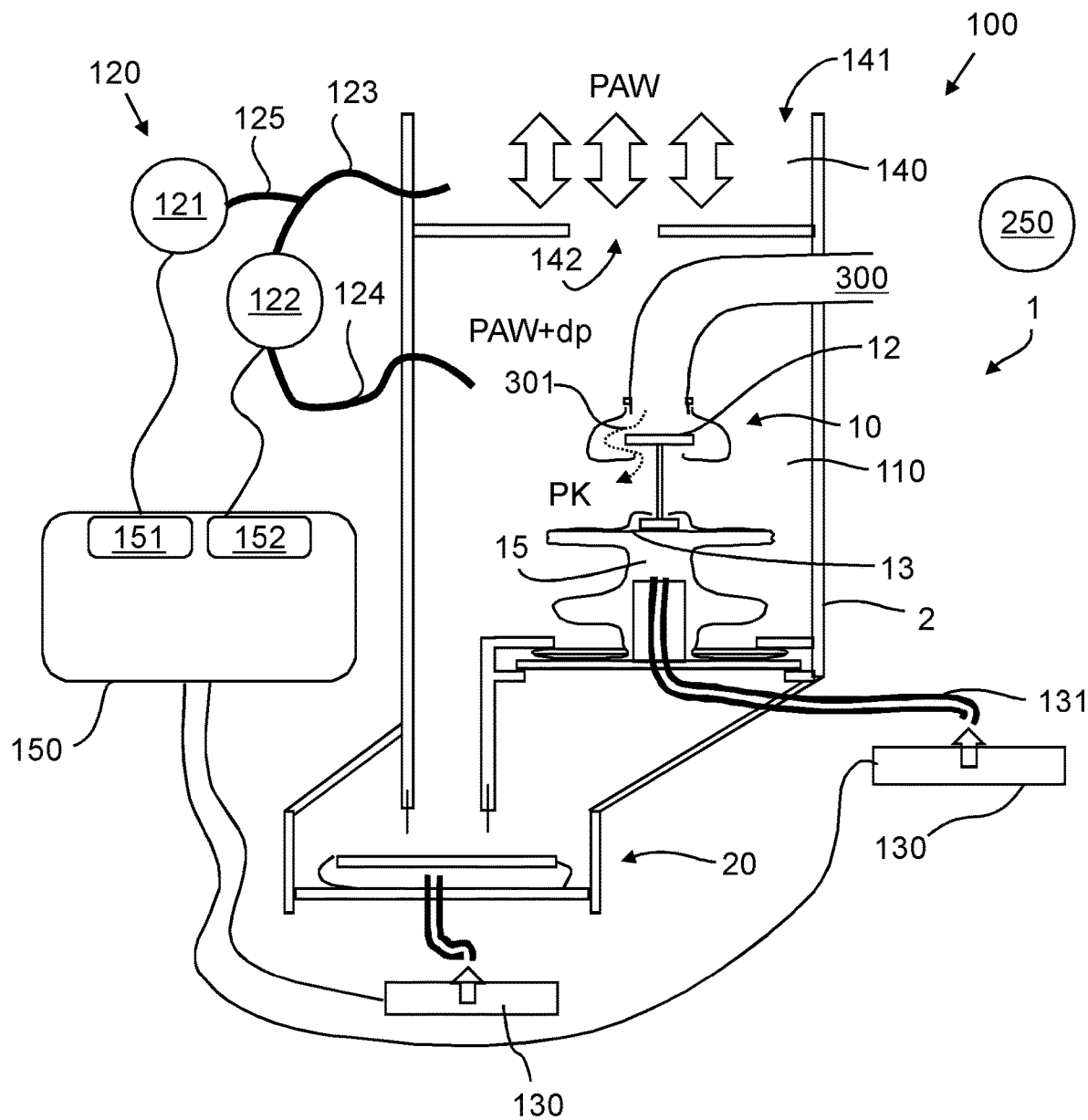
FIG. 6 is a schematic view of parts of a ventilation system according to the present invention.

FIGS. 4 and 6 show the device 1 according to the present invention according to the open position 310 with further details.

Further, a mechanical transmission device 13 of the inhalation valve 10 is provided, which is connected via a mechanical connection element 14 to the closing element 12 in order to hold the closing element 12 in a starting position of the transmission device 13 in the closed position 320, preferably such that the inhalation valve 10 is provided as a normally closed inhalation valve 10 for the ventilation system 100.

A control pressure source 130 is configured in the exemplary embodiments concretely as a pump 130, and the explanations given concerning these exemplary embodiments are not limited to this concrete embodiment. The pump 130 may be used to provide a control pressure PS in a control pressure chamber 15 for the transmission device 13 in order to move the transmission device 13 by the control pressure PS, especially by an increase in the control pressure PS, from the starting position. The transmission device 13 may be configured for the force-transmitting coupling of the pressure chamber 110 with the closing element 12, so that the closing element 12 is moved, outside of the starting position of the transmission device 13 and especially against the control pressure PS, in the direction of the closed position 320 in case of an increase in a chamber pressure PK in the pressure chamber 110. It can be seen in FIGS. 4 and 6 that the transmission device 13 may be arranged for this purpose such that it adjoins the pressure chamber 110, so that the chamber pressure PK can act on the first area S1 of the transmission device 13. For example, an opening of the inhalation valve 10 is provided for this purpose in order to expose the transmission device 13 to the chamber pressure PK. The first area S1 may be used here to admit the chamber pressure PK from the pressure chamber 110 in order to convert the increase in the chamber pressure PK into an increasing force for moving the closing element 12 in the direction of the closed position 320, and thus for the force-transmitting coupling.

In addition to the first area S1, the transmission device 13 may further have a second area S2 for admitting the control pressure PS from the control pressure chamber 15 in order to convert an increase in the control pressure PS into an increasing force for moving the closing element 12 in the direction of the open position 310. It is shown in FIGS. 4 and 6 that the transmission device 13 may be arranged adjoining the control pressure chamber 15 for this purpose as well. Moreover, the transmission device 13 may also be used to separate the control pressure chamber 15 from the pressure chamber 110, preferably to separate it in a fluid-tight manner. The transmission device 13 may form for this purpose a limitation of the control pressure chamber 15, possibly together with additional walls of the control pressure chamber 15. These additional walls are configured, for example, in the form of an elastomer.

The first area and the second area, S1, S2, may preferably be arranged opposite each other, as the areas on the opposite sides of the transmission device 13, in order to convert the increase in the chamber pressure PK and in the control pressure PS into mechanical deflections of the transmission device 13 in opposite directions. The closing element 12 may have a closing element area S3 for closing the inhalation opening 11 in the closed position 320, the area ratio of the closing element area S3 to the first area S1 being in the range of 0.25 to 1, preferably in the range of 0.3 to 0.75, and preferably in the range of 0.5 to 0.6. By contrast, the surface area of the second area S2 may correspond to the surface area of the first area S1 or differ from this by up to 10%.

The transmission device 13 may be rigidly connected to the closing element 12 via the connection element 14 in order to move the closing element 12 from the open position 310 into the closed position during the increase in the chamber pressure PK, especially during an increase in the airway pressure PAW, which takes place because of an exhalation process, and to hold it closing device in the closed state in the closed position 320 after the movement and/or in the starting position of the transmission device 13.

In addition, the transmission device 13 may be configured in the form of a diaphragm 13, especially a pressure diaphragm, preferably in order to provide a movement of the closing element 12, and especially the force-transmitting coupling, by a mechanical deflection of the diaphragm 13 as a function of an increase in the control pressure PS and/or in the chamber pressure PK, the diaphragm 13 being connected to the closing element 12 for transmitting the deflection to the closing element 12 via the connection element 13.

According to the views shown in FIGS. 4 and 6, the transmission device 13 is configured to provide a functionality of a normally closed inhalation valve in the starting position in the absence of control pressure PS, i.e., without the provision of the control pressure PS.

In addition, a control device 150 may be provided according to FIG. 6 for an automatic control and/or regulation of the flow 301 in order to determine the control pressure PS for moving the closing element 12 in the direction of the open position 310 and in order especially to provide the control pressure PS competitively with the chamber pressure PK in the pressure chamber 110, so that the movement of the closing element 12 preferably depends on a ratio of the control pressure PS to the chamber pressure PK. In addition, an auxiliary pressure chamber 140 is provided in this case for passing on the provided breathing gas 300 to the patient 200, the auxiliary pressure chamber 140 being connected to the pressure chamber 110 via a diaphragm opening 142 in a fluid-communicating manner, and wherein at least one sensor array 120 is provided in order to detect an actual pressure difference dP prevailing between the auxiliary pressure chamber 140 and the pressure chamber 110, the control device 150 being configured to determine a deviation of a desired pressure difference between the auxiliary pressure chamber 140 and the pressure chamber 110 and the detected actual pressure difference dP in order to determine the control pressure PS as a function of the deviation.

FIGS. 3 and 6 show parts of a ventilation system 100 according to the present invention for ventilating a patient 200 by means of a breathing gas 300, wherein the ventilation system 100 has a gas source 250 for providing the breathing gas 300, a device 1 according to the present invention with an inhalation valve 10 in the form of a normally closed inhalation valve 10 and a normally open exhalation valve 20.

Further exemplary embodiments of the device 1 according to the present invention and of the ventilation system 100 according to the present invention, which represent an optional variant of the above-mentioned embodiments of the present invention, will be described in the following description of the present invention.

According to FIG. 3, the ventilation system 100 may also be, for example, in the form of a ventilator 100 or anesthesia apparatus. A valve block 2 as a part of the ventilation system 100 may have here at least the following parts, and possibly combine them as an assembly unit comprising:
- the inhalation valve 10,
- the pressure chamber 110, especially in the form of a main pressure chamber, and
- the exhalation valve 20.

The inhalation valve 10 and the exhalation valve 20 are conventionally configured as normally open valves, i.e., they are opened without admission of pressure or other energy. Such a conventional inhalation valve 10 possibly also has the full functionality. However, the control characteristic does not correspond now to that of a self-stabilizing pressure controller. The inhalation valve 10 may deviate according to the present invention from this configuration.

An inlet 16, which is connected via a tube to a gas supply unit of a gas source 250, may be provided for the inhalation valve 10. An outlet 26, which may optionally be connected to an exhalation tube, may correspondingly be provided for the exhalation valve 20.

The valve block 2 may have, in addition, the ventilation opening 141. A ventilation mask or a tube, with which the patient 200 is ventilated, may be connected to the ventilation opening 141.

As is shown in FIG. 4, the closing element 12 may be held in a holding element 17 having a bell-shaped configuration, and a circumferential closing edge 18 formed at the bottom of the holding element 17 forms the inhalation opening 11 for the breathing gas 300 for passage into the pressure chamber 110 of the valve block 2. The breathing gas 300 may be provided by the gas source 250. Further, the chamber pressure PK may correspond to the airway pressure PAW in the example shown. The chamber pressure PK can be determined by the pressure of the breathing gas 300 during inhalation and by the exhalation pressure of the patient 200 during exhalation.

Moreover, the closing element area S3 of the closing element 12 is shown. An area enclosed by the closing edge 18, hereinafter also called crater area (valve seat), may approximately correspond to the surface area of the closing element area.

The transmission device 13 may have two opposite sides, with a first area S1 and—opposite this—with a second area S2. The first area S1 may face the pressure chamber 110 in order for the chamber pressure PK to be admitted to it. The second area S2 may face the control pressure chamber 15 in order for the control pressure PS to be admitted to it. The chamber pressure PK will then act on the area S1 as the outer side of the transmission device 13, and, depending on the ratio of the chamber pressure PK to the control pressure PS, it can bring about a mechanical deflection of the transmission device 13.

The connection element 14 may be connected on one side to the outer side of the transmission device 13 at the first area S1, and it may be connected on an opposite side to the closing element 12. The connection element 14 makes it thus possible to convert the mechanical deflection of the transmission device 13 into a movement of the closing element 12. An increase in the chamber pressure PK is thus converted into the deflection of the transmission device 13, and the deflection of the transmission device 13 is converted into the movement of the closing element 12 in the direction of the closed position 320.

Arrow 301 shows the flow 301 of the breathing gas 300 in the manner of a gas stream during inhalation. The breathing gas 300 flows in this manner first into the pressure chamber 110 and then to the patient 200. In order to control at least the flow 301 for a ventilation of the patient 200, a control and/or regulation of the inhalation valve 10 may be provided. The inhalation valve 10 has the advantage that it can be used for controlling and/or regulating the ventilation with pneumatically driven valves 10, 20, which are arranged close to the patient and have stable working points. This makes possible an improved regulation of a constant chamber pressure PK, especially of the airway pressure PAW, due to the optimized configuration of the inhalation valve 10.

The inhalation valve 10 is advantageously configured such that an increasing chamber pressure PK exerts an increasing force on the inhalation valve 10, especially on the closing element 12. The inhalation valve 10 can thus independently compensate a chamber pressure PK, which thus represents a pressure equivalent of the control pressure PS of the pump 130. As a result, slow pressure settings require only a slow regulation or in the extreme case only a control without returning the chamber pressure PK. In other words, the regulation of the inhalation valve 10 may be carried out at least partially by the inhalation valve 10 itself.

An advantageous NC (Normally Closed) inhalation valve 10 located close to the patient with control or regulation may thus be obtained for ventilation purposes, where "close to the patient" means, for example, that the distance from the patient is, for example, less than 0.5 m or 0.25 m (meter).

Figure 5:
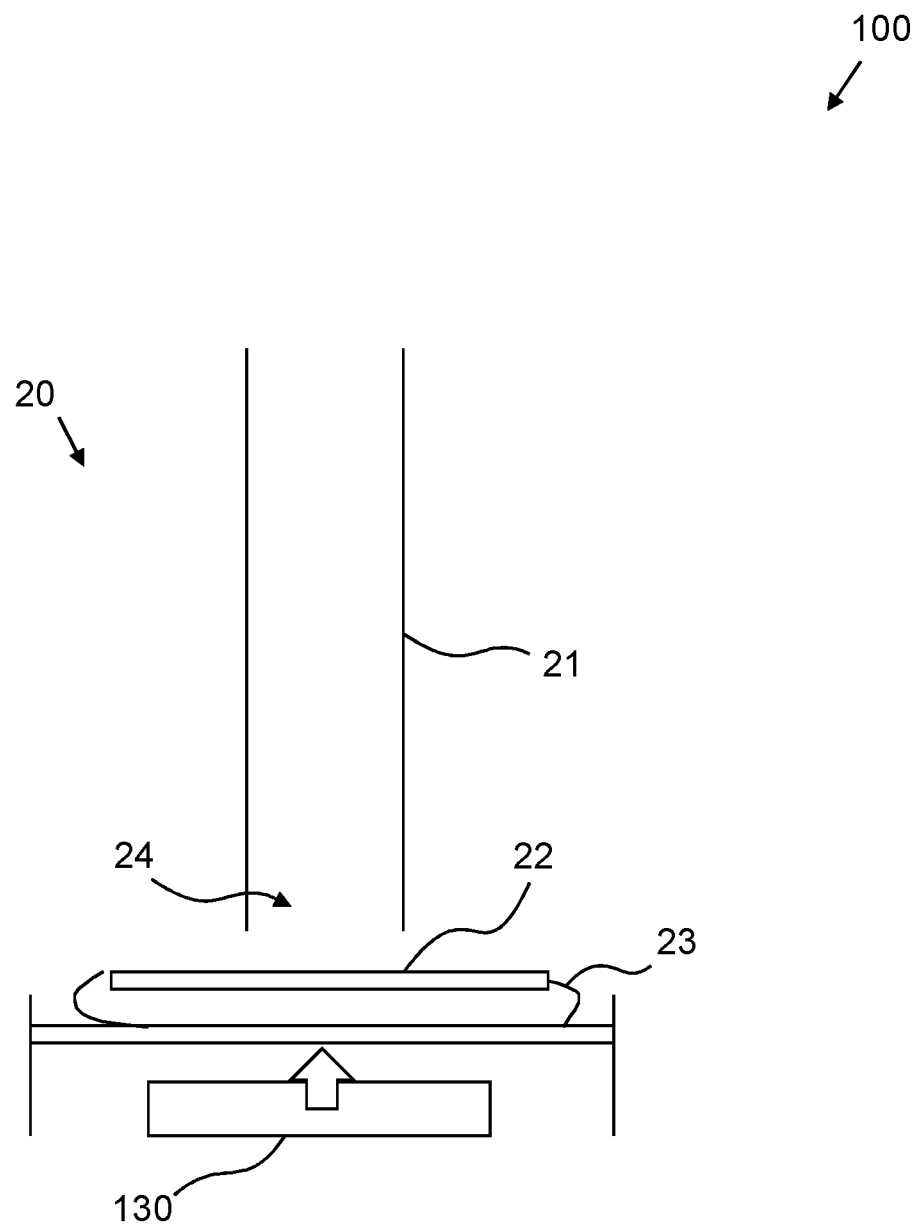
FIG. 5 is a schematic view of an exhalation valve of a ventilation system according to the present invention.

FIG. 5 shows an exhalation valve 20 (exhalation valve) of a ventilation system 100 according to the present invention. This exhalation valve may have a port 21 for forming an exhalation opening 24, a closure 22 for closing the exhalation opening 24 as well as a chamber wall 23 for forming a chamber for the exhalation valve 20. The additional pump 130 (which is provided in addition to the pump 130 for the inhalation valve 10) may generate a pump pressure in the chamber, by which the closure is pushed into the exhalation opening 24 of the port 21 and which thus closes the exhalation valve 20. The exhalation valve 20 is thus a normally open valve, i.e., NO (normally open). With the exhalation valve 20 opened, an exhalation air stream, which arrives from the patient 200, can be discharged through the exhalation valve 20 from the valve block 2 to the outside into the ambient air or into a recycling system, which can be used especially in anesthesia ventilation systems 100 but also in ventilators 100 without anesthesia function.

An excessively high chamber pressure PK of the pressure chamber 110 of the valve block 2 may lead to an opening process in the exhalation valve 20, as a result of which an escape of the breathing gas 300 and hence a reduction of the chamber pressure PK are made possible. The exhalation valve 20 is thus a self-regulating valve, which can nevertheless be regulated for a higher dynamics.

FIG. 6 pertains to another view of a ventilation system 100 according to the present invention with a device 1 according to the present invention, which comprises an inhalation valve 10. It is shown that the valve block 2 forms the pressure chamber 110. The chamber pressure PK in the pressure chamber 110 can influence the inhalation valve 10 by the chamber pressure PK being admitted to the transmission device 13. Further, a control pressure PS, which is generated by the pump 130 for controlling and/or regulating the ventilation system 100, especially the inhalation valve 10, may also be admitted to the transmission device 13 in a direction opposite the chamber pressure PK. The pump 130 is connected for this purpose to a control pressure chamber 15 via a pump tube 131 in a fluid-communicating manner. As an alternative, the pump 130 may be fastened to the inhalation valve 10, preferably via a coupling element, so that the device 1 according to the present invention may be configured, in particular, as an assembly unit. The explanations given in connection with this exemplary embodiment also pertain to this variant. In the example shown, the chamber pressure PK may essentially correspond to an airway pressure PAW, possibly with a deviation dp. This deviation thus represents an actual pressure difference dP between the airway pressure PAW and the chamber pressure PK, which may optionally be analyzed for the control and/or regulation.

Figure 7:
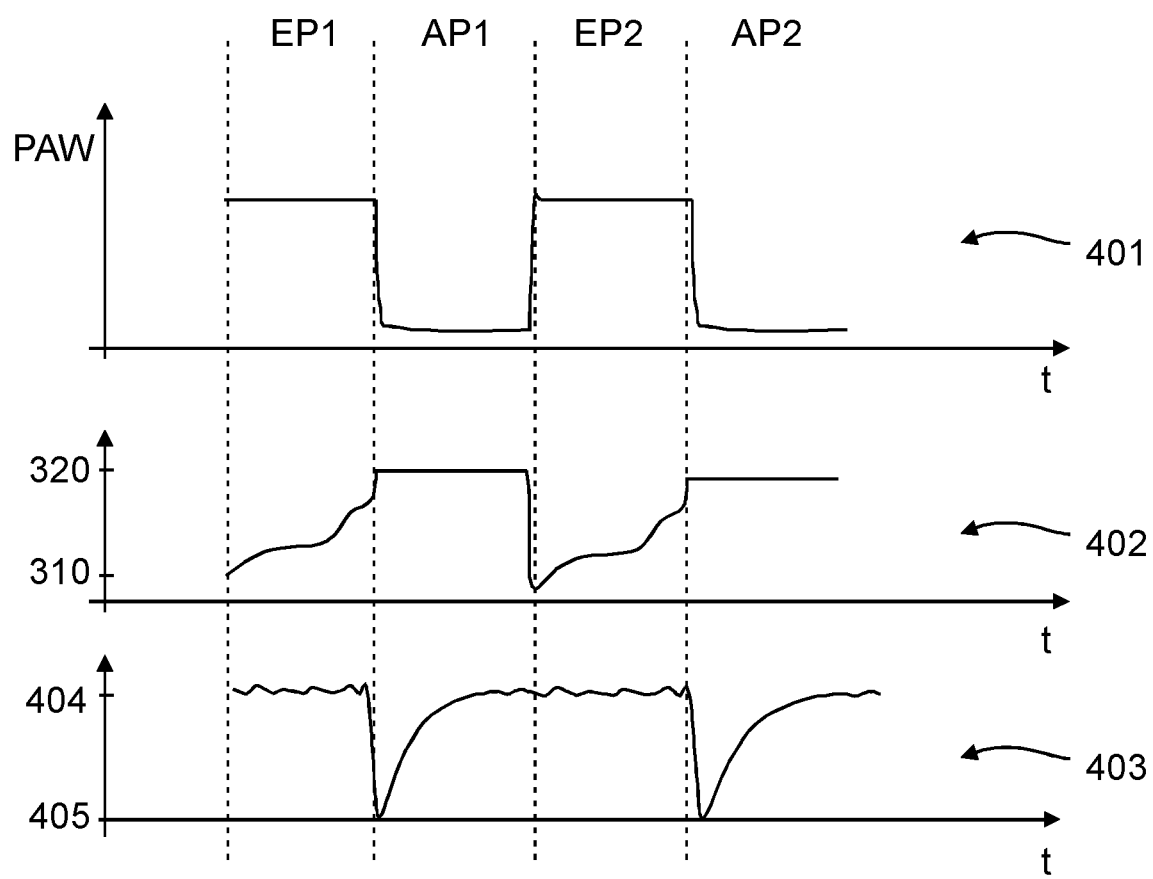
FIG. 7 is a graph showing a curve of the patient's airway pressure over time correlated with the position of the inhalation valve over time and the position of the diaphragm of the exhalation valve over time.

FIG. 7 shows a first coordinate system 401 for illustrating an exemplary curve of the airway pressure PAW over the time t. Furthermore, a second coordinate system 402 is shown for illustrating a curve describing the position of the transmission device 13 of the inhalation valve 10 over the time t. If the transmission device 13 is configured as a diaphragm 13, the position of the transmission device 13 may be represented in the form of an extent of the deflection of the transmission device 13. The position of the transmission device 13 is correlated with—and is, for example, proportional to—the position of the closing element 12. The positions of the transmission device 13, in which the closing element 12 is in the closed position 320 and in the open position 310, are therefore marked in the second coordinate system 402. The curve describing a state of the exhalation valve 20 over the time t is shown in a third coordinate system 403. The curve begins here with the closed position 404 of the exhalation valve 20 and passes over into the open position 405 of the exhalation valve 20.

Moreover, the inhalation phases EP1, EP2, which are provided during the ventilation or the regulation of the ventilation system 100 and which alternate periodically with the exhalation phases AP1, AP2, which are likewise shown, are shown in the coordinate systems 401, 402, 403.

The curve describing the airway pressure PAW may be provided here as follows: The airway pressure is at a first high value during the inhalation phases EP1, EP2 and it is at a value that is lower compared to the first value during the exhalation phases AP1, AP2.

The curve describing the position of the transmission device 13 of the inhalation valve 10 and in the same manner the curve describing the position of the closing element 12 may be as follows over the time t: Rising during the inhalation phases EP1, EP2 from a first position value (open position 310) to a second value (closed position 320) that is higher compared to the first value, and remaining during the exhalation phases AP1, AP2 at a higher value, e.g., at the value reached at the end of the inhalation phase EP1, EP2. In other words, the inhalation valve 10 may be wide open at the beginning of the inhalation phase EP1, EP2 and then closed to a greater or lesser extent until the end of the respective inhalation phase EP1, EP2. This means in the case of a normally closed inhalation valve 10 that the control pressure must be increased at the beginning during the inhalation phase EP1, EP2 in order to bring about the opening. The inhalation valve 10 is closed during the exhalation phases AP1, AP2, so that no additional control pressure PS needs to be applied here in the case of a normally closed inhalation valve.

The curve describing the state of the exhalation valve 20 over the time t is shown as follows: At a comparatively high first value (closed 404) during the inhalation phases EP1, EP2 and sharply falling during the inhalation phases EP1, EP2 to a low value (open 405) and then rising again comparatively rapidly.

A target value for the airway pressure PAW during inhalation may be, for example, a constant pressure with a higher values of, for example, 20 mbar or 25 mbar. During exhalation, the target value for the airway pressure PAW may likewise be, for example, a constant pressure value, which is, however, much lower than the target value during inhalation. For example, the target value may be 4 mbar to 5 mbar during exhalation.

A control device 150 shown in FIG. 6 may be used to control and/or regulate the curves shown in FIG. 7. This control device 150 may actuate for this purpose, for example, the pump 130 for controlling the inhalation valve 10 and/or the additional pump 130 for controlling the exhalation valve 20. To influence the position of the closing element 12 of the inhalation valve 10 within the framework of the control and/or regulation, the pump 130 may generate the control pressure PS in a control pressure chamber 15, as it is also illustrated in FIG. 6. The pump 130 is always configured, for example, as a micropump, especially on the basis of a piezo ceramic. The necessary speed of the pressure regulation determines the quality of the pressure regulation for the ventilation and may be lower than 10 msec (milliseconds) and may not exceed 50 msec depending on the requirements.

In addition, the auxiliary pressure chamber 140 may be provided, which is arranged adjoining the pressure chamber 110 (as the main pressure chamber 110). The auxiliary pressure chamber 140 may be connected via the diaphragm opening 142 to the (main) pressure chamber 110 in a fluid-communicating manner for the exchange of breathing gas 300. Moreover, the ventilation opening 141 of the auxiliary pressure chamber 140 may be provided in order to ventilate the patient 200 with the breathing gas 300. The ventilation opening 141 may be formed in a wall of the valve block 2. The breathing gas 300 can reach the patient 200 through the ventilation opening 141 from the auxiliary pressure chamber 140 as inhaled gas and it can enter the auxiliary pressure chamber 140 as exhaled gas from the patient 200. The pressure in the auxiliary pressure chamber 140 may correspond especially to the airway pressure PAW, and the chamber pressure PK in the pressure chamber 110 may correspond to the airway pressure PAW with a deviation of dp.

Important ventilation parameters or operating parameters to be regulated or controlled are, for example as follows:

the gas flow (flow), the chamber pressure PK in the pressure chamber, the concentration of carbon dioxide $CO_2$, and the concentration of oxygen $O_2$.

As is also shown in FIG. 6, the sensor array 120 may be provided for the control and/or regulation. This is arranged, for example, at least partially in the pressure chamber 110 or—corresponding to the exemplary embodiment, outside the pressure chamber 110, but in a fluid-communicating manner with said pressure chamber 110. The sensor array 120 comprises, in particular, a first sensor 121 for detecting the airway pressure PAW in the auxiliary pressure chamber 140 and a second sensor 122 for detecting the flow rate (flow) between the auxiliary pressure chamber 140 and the pressure chamber 110. The second sensor 122 may also be defined as a differential pressure sensor, which detects the actual pressure difference dP between the pressure chamber 110 and the auxiliary pressure chamber 140. The pressure drop over the diaphragm opening 142, which is detected as an actual pressure difference dP with the second sensor 122, corresponds here to the flow flowing through the diaphragm opening 142. The values detected by the sensors 121, 122 can be sent to the controller.

The regulation of the ventilation system 100 or of the inhalation valve 10 may serve the purpose of ensuring the simplest possible, robust, stable and tolerant pressure regulation. Table 1a below shows exemplary requirements on the inhalation valve 10.

|   | Phase | Dynamics | Position | Property |
|---|---|---|---|---|
| 1 | Standby | Low | Closed | Gas consumption, leakage allowed |
| 2 | Standby/ stop/restart | Low | Opens | Slow opening (adaptation) |
| Ph3 | Start of inhalation | High | Opens | Wide opening for high flow |
| Ph4 | Regulation of inhalation | Medium | Open-closed | PAW vs. pump |
| Ph5 | Start of exhalation | Medium | Closes | Slight crossflow |
| Ph6 | Regulation of exhalation | Medium | Closed | Compensation of leakage through mask |

Table 1b below shows exemplary requirements on the exhalation valve 20.

|   | Phase | Dynamics | Position | Property |
|---|---|---|---|---|
| 1 | Standby | Low | Closed |  |
| 2 | Standby/ stop/restart | Low | Closed |  |
| Ph3 | Start of inhalation | Low | Closed | Reliable closing |
| Ph4 | Regulation of inhalation | Medium | Closed | Possible compensation if PAW is too high (coughing) |
| Ph5 | Start of exhalation | Very high | Opens | Large cross section |
| Ph6 | Regulation of exhalation | Medium | Open - closed | PAW vs. pump |

It is shown in FIG. 6 that the second sensor 122 may be connected to the auxiliary pressure chamber 140 via a first fluid line 123 and to the (main) pressure chamber 110 via a second fluid line 124. The second sensor 122 can detect in this manner the actual pressure difference dP between the pressure chamber 110 and the auxiliary pressure chamber 140. In addition, a third fluid line 125 branches off from the first fluid line 123 and leads to the first sensor 121. This makes it possible to detect the airway pressure PAW by the first sensor 121. In order to send the pieces of information determined for the actual pressure difference dP and the airway pressure PAW during the detection to the controller, the sensors 121, 122 may be connected to the control device 150 for the transmission of the information. A first control unit 151 can detect the information of the first sensor 121, and a second control unit 152 can detect the information of the second sensor 122. The pieces of information detected can be analyzed by the control device 150, and the respective pump 130 of the inhalation valve 10 and the exhalation valve 20 can be actuated by the control device 150 corresponding to the analysis.

This actuation can cause in the inhalation valve 10 the pump 130, which is connected to the control pressure chamber 15 via a pump tube 131, to generate a control pressure PS in the control pressure chamber 15. The inhalation valve 10 may be configured structurally such that an opening and closing of the inhalation valve 10, i.e., of the closing element 12, may occur solely due to the pressure ratios between the chamber pressure PK and the control pressure PS. The position of the transmission device 13, especially diaphragm 13, can thus be adjusted such that an equilibrium of forces will develop. An inlet pressure from the gas source 250, which pressure brings about the flow 301 of the breathing gas 300, may have a constant value now, e.g., 50 mbar.

When imagining transmission devices 13 of an ideal form, i.e., without own force per displacement and without damping (force per velocity), an additional regulation might not possibly be necessary. Real transmission devices 13 do, however, require a force in order to move out of their zero position. This corresponds to a type of spring characteristic.

Very rapid movements can likewise be hindered by the damping. The opposing forces, which develop due to the damping, i.e., usually due to flexing of the elastomer, possibly lead to a reduction of the driving forces and result in a type of velocity limitation. Abrupt pressure changes, which are required, for example, by the airway pressure PAW (coughing) or the control pressure PS (start of inhalation or exhalation), may possibly lead only to a slowed-down movement of the transmission device 13 and hence to a limitedly rapid compensation of the pressure ratios.

It is especially useful for this reason to carry out a regulation of the control pressures. As a result, substantially more rapid compensation processes may be possible than in the case of a control without returning the airway pressure PAW. The controller provided by the control device 150 may possibly deal here only with the compensation of sudden events. A permanent readjustment of the unstable working point will be eliminated in that case.

If the transmission device 13 is configured as a diaphragm, the diaphragm area may have a diameter of 20 mm. The crater area of the inhalation valve 10 may have, for example, a diameter of 8 mm. The ratio of the diaphragm area to the crater area can influence the behavior of the inhalation valve 10 with respect to the closing as a function of the ratio of the chamber pressure PK to the control pressure PS. This is illustrated as an example on the basis of the following formula, where AM is the diaphragm area, PEIN is the inlet pressure from the gas source and AK is the crater area (PEN brings about a force at the closing element 12 in the direction of the closed position 320):

$$AK*PEIN+AM*PAW-AM*PS=0 \text{ (equilibrium of forces).}$$

The formula yields $$PAW=PS-PEIN*AK/AM$$

as a result of rearrangement.

An exemplary desired variable is obtained for the airway pressure PAW=17 mbar with PEIN=50 mbar.

The control device 150 may advantageously be configured to perform a rapid adjustment of the airway pressure PAW to such a desired variable for the airway pressure PAW. The control device 150 may correspondingly be configured to set the control pressure PS by means of the controller such that the airway pressure PAW preset (according to the desired variable) is set for the patient 200. The desired variable may also be subject to great changes in the course of the ventilation cycles, possibly also due to interaction with the patient 200. This likewise leads to the requirement for the regulation to compensate these interference variables.

Due to the detection of the second sensor 122, which detection is provided in the example shown, the sum of the airway pressure PAW+actual pressure difference dP (i.e., PAW+dp) is available. The actual pressure difference dP may be positive now during inhalation (volume flow to the patient) and negative during exhalation.

Figure 8:
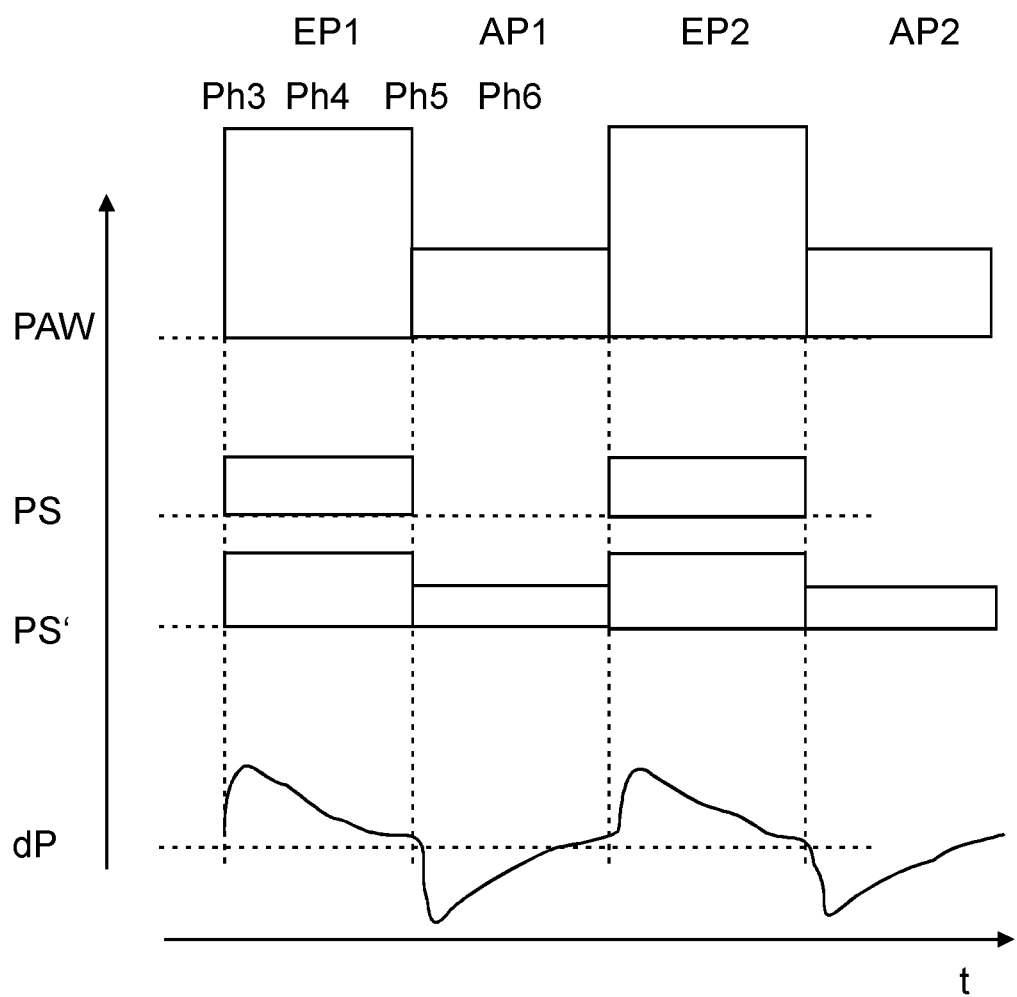
FIG. 8 is a graph showing an exemplary curve of manipulated variables over time for the control pressure of the inhalation valve and of the exhalation valve.
Figure 9:
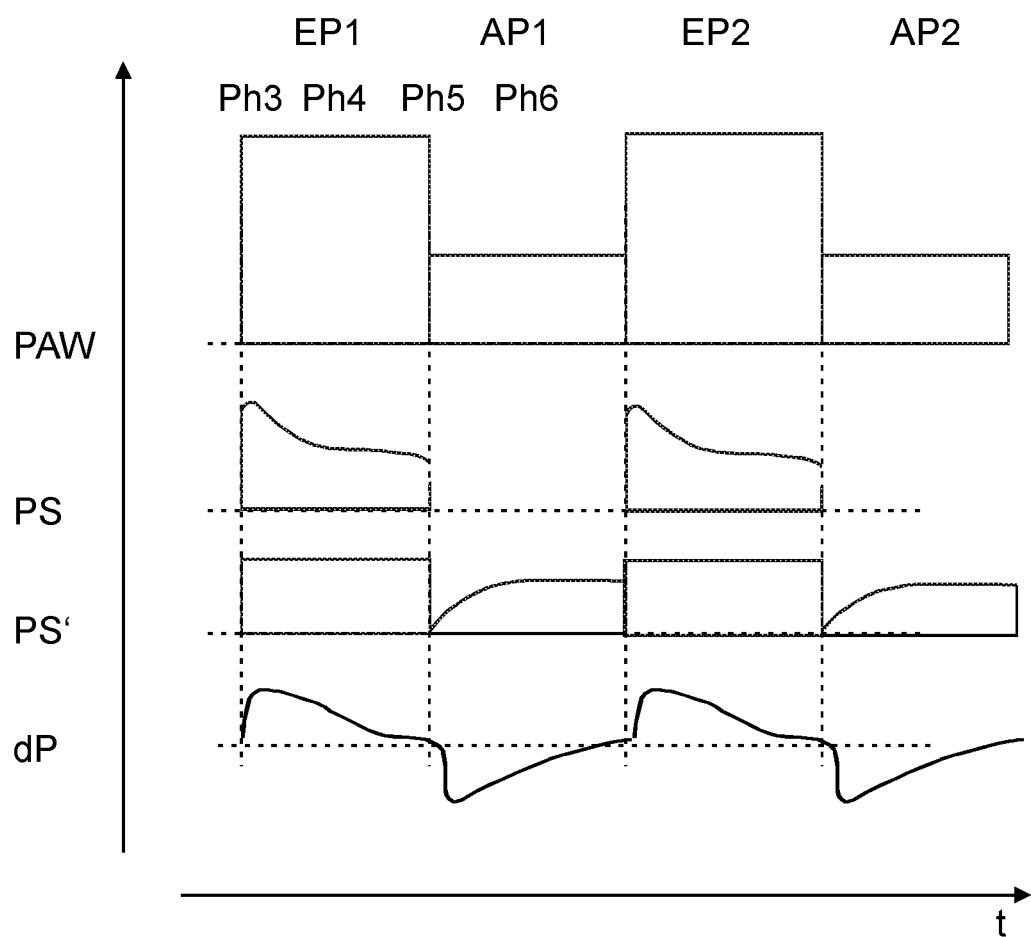
FIG. 9 is a graph showing another exemplary curve of manipulated variables over time for the control pressure of the inhalation valve and of the exhalation valve.
Figure 10:
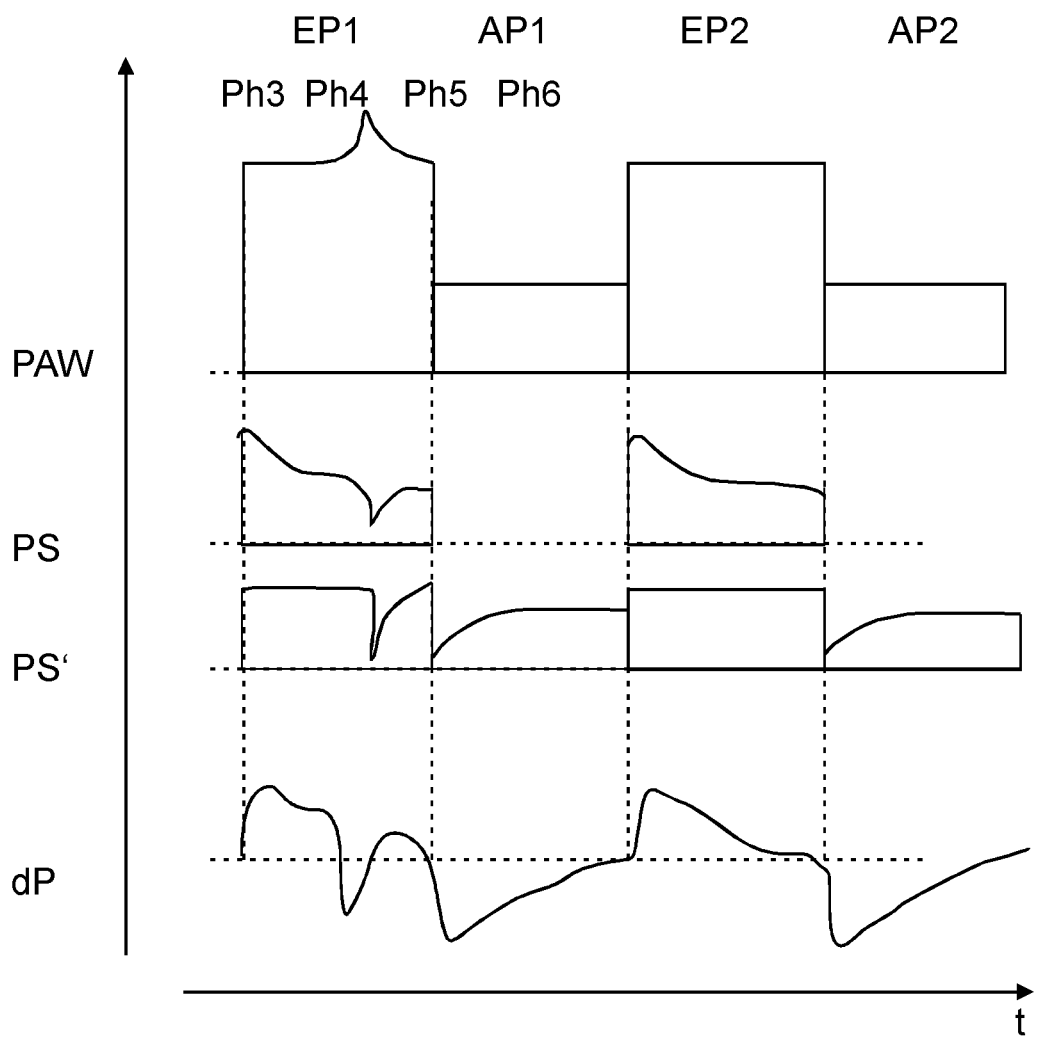
FIG. 10 is a graph showing another exemplary curve of manipulated variables over time for the control pressure of the inhalation valve and of the exhalation valve.

For further illustration, FIGS. 8 through 10 show each an exemplary regulation. The curve describing the control pressure PS, which is generated in the inhalation valve 10 by the pump 130 (over the time t), is shown in all cases. Further, the changes over time in another control pressure PS', which control pressure PS' is used to actuate the exhalation valve 20, are shown. Moreover, the changes over time in the airway pressure PAW (e.g., as an actual value of the airway pressure PAW detected by the first sensor 121) and in the flow according to the actual pressure difference dP are shown. The time axis comprises, for example, a time range from 0 sec to 12 sec, the vertical broken lines marking 3-second intervals. Moreover, the inhalation phases EP1, EP2 are shown again, which alternate periodically with the exhalation phases AP1, AP2, which are shown as well. Moreover, the partial phases Ph3 through Ph6 are marked corresponding to Tables 1a, 1b:

Partial phase Ph3—start of inhalation,
Partial phase Ph4—regulation of inhalation,
Partial phase Ph5—start of exhalation, and
Partial phase Ph6—control/regulation of exhalation.

FIG. 8 shows an exemplary control, in which the control pressure PS for the inhalation valve 10 and the additional control pressure PS' for the exhalation valve 20 are set without returning the airway pressure PAW to the control device 150.

If a control is used instead of a regulation, the first and second sensors 122 and possibly also the auxiliary pressure chamber 140 may not be necessary.

The changes over time in the control pressure PS at the inhalation valve 10 may be selected as follows: For example, 20 mbar during the inhalation phases EP1, EP2 and, for example, 0 mbar during the exhalation phases AP1, AP2.

When using the control (open loop), the changes over time in the additional control pressure PS' at the exhalation valve 20 may be selected as follows: For example, 25 mbar during the inhalation phases EP1, EP2 and, for example, 4 mbar during the exhalation phases AP1, AP2.

The shown changes over time in the volume flow, which are seen in an actual pressure difference dP, are not possibly relevant for the control (open loop).

FIG. 9 shows an exemplary regulation, in which the control pressure PS for the inhalation valve 10 and the additional control pressure PS' for the exhalation valve 20 are set without returning the airway pressure PAW to the control device 150. Unlike in the example shown in FIG. 8, a so-called "flow compensation" may, however, be used here within the framework of the regulation. The actual pressure difference dP is compensated here by the control device 150. The changes over time in the control pressure PS at the inhalation valve 10 are correspondingly obtained from a superimposition of the "controlled" curve (shown in FIG. 8) and a regulation component for compensating the actual pressure difference dP.

This superimposition may lead, furthermore, at the beginning of the inhalation phases EP1, EP2 to a maximum of the control pressure PS, which is, for example, greater than 25 mbar, and at which the inhalation valve 10 is opened especially wide in order to reach the airway pressure PAW of 25 mbar in a short time. The control pressure PS for actuating the inhalation valve 10 may continue to be 0 mbar during the exhalation phases AP1, AP2.

The curve describing the course over time of the additional control pressure PS' at the exhalation valve 20 corresponds, especially during the inhalation phases EP1, EP2, to the curve shown on the basis of FIG. 8, because the control continues to be present. However, the regulation of the actual pressure difference dP is superimposed to the control of the exhalation valve 20 during the exhalation phases AP1 and AP2, and the curve describing the actual pressure difference dP has a minimum. To regulate the actual pressure difference dP to the value 0 as rapidly as possible during exhalation, the exhalation valve 20 may be opened more wide by pressure reduction than is preset by the control (open loop) alone. A pressure increase rising approximately linearly from the value 0 is obtained for the additional control pressure PS' up to 4 mbar.

The curve describing the volume flow over time, which is manifested in the actual pressure difference dP, is as follows: The actual pressure difference dP rises rapidly during the inhalation phases EP1, EP2 to a maximum 612, from which it drops again approximately linearly to 0 mbar actual pressure difference dP at the end of the respective inhalation phase EP1, EP2. The volume flow or gas flow reverses during the exhalation phases AP1, AP2 and is directed now away from the patient 200. The reversal of the direction is manifested in a change in the sign of the actual pressure difference dP, which rapidly reaches therefore a minimum 616 at the beginning of the exhalation phases AP1, AP2 in order to rise thereafter linearly, also supported by the regulation, to the value 0.

FIG. 10 shows an exemplary regulation, in which the control pressure PS for the inhalation valve 10 and the additional control pressure PS' for the exhalation valve 20 are set such that the airway pressure PAW is returned to the control device 150. A flow compensation may likewise be provided here by the control device 150. A pressure increase, which may develop, for example, due to a cough event (see peak in the curve during the partial phase Ph4), is superimposed here to the curve describing the airway pressure PAW over time. The regulation has the advantages over the control that such a pressure increase can be dealt with in an improved manner.

The pressure increase in the airway pressure PAW possibly also leads to an increase in the chamber pressure PK in the pressure chamber 110. The control device 150 may be configured to carry out the regulation with respect to the pressure increase as described below:

The volume flow according to the actual pressure difference dP suddenly reverses, so that a minimum develops during the inhalation phase EP1 (in partial phase Ph4). The regulation compensates on the basis of the detection of the second sensor 122 and generates a pressure drop at a minimum of the control pressure SP for the control pressure chamber 15 (likewise during partial phase Ph4), which control pressure SP closes the inhalation valve 10 even more, which leads to a throttling of the flow 301 and hence also to a pressure reduction in the pressure chamber 110, and/or the first sensor 121 likewise detects the pressure increase brought about in the airway pressure PAW by the cough event during inhalation. The regulation compensates by lowering the additional control pressure PS' at a minimum (during the partial phase Ph4) and thus opens the exhalation valve 20, which leads to a more rapid pressure drop in the pressure chamber 110.

It is seen that a cough event occurring during the regulation (closed loop) can be reliably compensated in this manner.

The above explanation of the embodiments describes the present invention exclusively within the framework of examples. Individual features of the embodiments, if technically meaningful, may, of course, be freely combined with one another without going beyond the scope of the present invention.

While specific embodiments of the invention have been shown and described in detail to illustrate the application of the principles of the invention, it will be understood that the invention may be embodied otherwise without departing from such principles.

1 Device, valve device
2 Valve block
10 Inhalation valve
11 Inhalation opening
12 Closing element
13 Transmission device, diaphragm
14 Connection element
15 Control pressure chamber
16 Inlet
17 Holding element
18 Closing edge
20 Exhalation valve
21 Port of 20
22 Closure of 20
23 Chamber wall of 20
24 Exhalation opening
26 Outlet
100 Ventilation system, ventilator
110 Pressure chamber
120 Sensor array
121 First sensor, of 120
122 Second sensor, of 120
123 First fluid line
124 Second fluid line
125 Third fluid line
130 Control pressure source, pump
131 Pump tube
140 Auxiliary pressure chamber
141 Ventilation opening
142 Diaphragm opening
150 Control device
151 First control unit of 150
152 Second control unit of 150
200 Patient
250 Gas source
300 Breathing gas
301 Flow
310 Open position
320 Closed position
401 First coordinate system
402 Second coordinate system
403 Third coordinate system
404 Closed position of 20
405 Open position of 20
dP Actual pressure difference
PAW Airway pressure
PK Chamber pressure
PS Control pressure
AP1 First exhalation phase
AP2 Second exhalation phase
EP1 First inhalation phase
EP2 Second inhalation phase
S1 First area
S2 Second area
S3 Closing element area
PS' Additional control pressure

What is claimed is:
1. A device comprising:
an inhalation valve for a ventilation system, the inhalation valve comprising:
a pressure chamber;
an inhalation opening for a flow of breathing gas into the pressure chamber to provide the breathing gas in the pressure chamber for the ventilation of a patient;
a closing element arranged movably, to close the inhalation opening to breathing gas flow in a closed position and to release breathing gas flow, at least partially, in an open position; and
a transmission device connected to the closing element via a connection element, to hold the closing element in the closed position in a starting position of the transmission device; and
a control pressure chamber with a control pressure source providing a control pressure in the control pressure chamber cooperating with the transmission device to move the transmission device by the control pressure out of the starting position based on the control pressure, wherein the transmission device is configured for a force-transmitting coupling of a pressure of the pressure chamber with the closing element, so that the closing element, in a position other than the closed position, is moved in the direction of the closed position during a rise in a pressure chamber pressure in the pressure chamber.

2. A device in accordance with claim 1, wherein the transmission device further comprises:
   a first area for admitting the chamber pressure from the pressure chamber to convert the rise in the chamber pressure into an increasing force for moving the closing element in the direction of the closed position; and
   a second area for admitting the control pressure from the control pressure chamber to convert an increase in the control pressure into an increasing force for moving the closing element in the direction of the open position, wherein the first and second areas are arranged opposite each other to convert the rise in the chamber pressure into mechanical deflections of the transmission device in one direction and to convert a rise in the control pressure into mechanical deflections of the transmission device in an opposite direction.

3. A device in accordance with claim 2, wherein:
   the closing element comprises a closing element area for closing the inhalation opening in the closed position;
   an area ratio of the closing element area to the first area is in the range of 0.25 to 1.

4. A device in accordance with claim 2, wherein the surface area of the second area corresponds to the surface area of the first area or differs from it by at most 10%.

5. A device in accordance with claim 1, wherein the transmission device is rigidly connected via the connection element to the closing element to move the closing element from the open position into the closed position during an increase in the chamber pressure in the pressure chamber during a pressure increase of an airway pressure, which takes place based on an exhalation process, and to hold the closing element closed, in the closed position, after the movement and/or in the starting position of the transmission device.

6. A device in accordance with claim 1, wherein:
   the transmission device is configured in the form of a diaphragm to provide a movement of the closing element by a mechanical deflection of the diaphragm as a function of an increase in the control pressure and/or the chamber pressure in the pressure chamber; and
   the diaphragm is connected to the closing element for transmitting the deflection to the closing element via the connection element.

7. A device in accordance with claim 1, wherein the transmission device is configured to provide a functionality of a normally closed inhalation valve when the control pressure fails to build up in the starting position.

8. A device in accordance with claim 1, wherein the control pressure source is configured as a piezo pump and sets the control pressure during an exhalation process of the patient in the range of 0 mbar to 3 mbar.

9. A device in accordance with claim 1, further comprising a control device configured to automatically control and/or regulate flow including to determine the control pressure for moving the closing element in the direction of the open position and to provide the control pressure relative to the chamber pressure in the pressure chamber, so that the movement of the closing element depends on a ratio of the control pressure and the chamber pressure.

10. A device in accordance with claim 9, further comprising:
    an auxiliary pressure chamber with a ventilation opening for passing on breathing gas from the pressure chamber to the patient, wherein the auxiliary pressure chamber is connected to the pressure chamber via a diaphragm opening in a fluid-communicating manner; and
    a sensor array configured to detect an actual pressure difference prevailing between the auxiliary pressure chamber and the pressure chamber, wherein the control device is configured to determine a deviation of a desired pressure difference between the auxiliary pressure chamber and the pressure chamber and the detected actual pressure difference to determine the control pressure as a function of the deviation.

11. A ventilation system for ventilating a patient with breathing gas, the ventilation system comprising:
    a gas source for providing the breathing gas;
    an exhalation valve configured as a normally open exhalation valve; and
    a device comprising
    an inhalation valve configured as a normally closed inhalation valve, the inhalation valve comprising:
       a pressure chamber;
       an inhalation opening for a flow of breathing gas into the pressure chamber to provide the breathing gas in the pressure chamber for the ventilation of a patient;
       a closing element arranged movably, to close the inhalation opening to breathing gas flow in a closed position and to release breathing gas flow, at least partially, in an open position; and
       a transmission device connected to the closing element via a connection element, to hold the closing element in the closed position in a starting position of the transmission device; and
    a control pressure chamber with a control pressure source providing a control pressure in the control pressure chamber cooperating with the transmission device to move the transmission device by the control pressure out of the starting position based on the control pressure, wherein the transmission device is configured for a force-transmitting coupling of a pressure of the pressure chamber with the closing element, so that the closing element, in a position other than the closed position, is moved in the direction of the closed position during a rise in a pressure chamber pressure in the pressure chamber.

12. A ventilation system in accordance with claim 11, wherein the transmission device further comprises:
    a first area for admitting the chamber pressure from the pressure chamber to convert the rise in the chamber pressure into an increasing force for moving the closing element in the direction of the closed position; and
    a second area for admitting the control pressure from the control pressure chamber to convert an increase in the control pressure into an increasing force for moving the closing element in the direction of the open position, wherein the first and second areas are arranged opposite each other to convert the rise in the chamber pressure into mechanical deflections of the transmission device in one direction and to convert a rise in the control pressure into mechanical deflections of the transmission device in an opposite direction.

13. A ventilation system in accordance with claim 11, wherein the transmission device is rigidly connected via the connection element to the closing element to move the closing element from the open position into the closed position during an increase in the chamber pressure in the pressure chamber during a pressure increase of an airway pressure, which takes place based on an exhalation process, and to hold the closing element closed, in the closed position, after the movement and/or in the starting position of the transmission device.

14. A ventilation system in accordance with claim 11, wherein:
the transmission device is configured in the form of a diaphragm to provide a movement of the closing element by a mechanical deflection of the diaphragm as a function of an increase in the control pressure and/or the chamber pressure in the pressure chamber; and
the diaphragm is connected to the closing element for transmitting the deflection to the closing element via the connection element.

15. A ventilation system in accordance with claim 11, wherein the transmission device is configured to provide a functionality of a normally closed inhalation valve when the control pressure fails to build up in the starting position.

16. A ventilation system in accordance with claim 11, wherein the control pressure source is configured as a piezo pump and sets the control pressure during an exhalation process of the patient in the range of 0 mbar to 3 mbar.

17. A ventilation system in accordance with claim 11, further comprising a control device configured to automatically control and/or regulate flow including to determine the control pressure for moving the closing element in the direction of the open position and to provide the control pressure relative to the chamber pressure in the pressure chamber, so that the movement of the closing element depends on a ratio of the control pressure and the chamber pressure.

18. A ventilation system in accordance with claim 17, further comprising:
an auxiliary pressure chamber with a ventilation opening for passing on breathing gas from the pressure chamber to the patient, wherein the auxiliary pressure chamber is connected to the pressure chamber via a diaphragm opening in a fluid-communicating manner; and
a sensor array configured to detect an actual pressure difference prevailing between the auxiliary pressure chamber and the pressure chamber, wherein the control device is configured to determine a deviation of a desired pressure difference between the auxiliary pressure chamber and the pressure chamber and the detected actual pressure difference to determine the control pressure as a function of the deviation.

19. A process for operating an inhalation valve of a ventilation system, the process comprising the steps of:
providing a pressure chamber;
initiating a flow of breathing gas through the inhalation opening of the inhalation valve into a pressure chamber to provide the breathing gas in the pressure chamber for ventilating a patient;
providing a closing element of the inhalation valve, which closing element is arranged movably, to close the inhalation opening to breathing gas flow in a closed position and to at least partially release the inhalation opening to breasting gas flow in an open position;
providing a transmission device of the inhalation valve, which transmission device is connected via a connection element to the closing element to hold the closing element in the closed position in a starting position of the transmission device, such that the inhalation valve is provided as a normally closed inhalation valve for the ventilation system; and
providing a control pressure chamber with a control pressure source to provide a control pressure in the control pressure chamber for the transmission device in order to move the transmission device by the control pressure out of the starting position based on the control pressure, wherein the transmission device is configured for the force-transmitting coupling of a pressure of the pressure chamber with the closing element, such that the closing element, in a position other than the closed position, is moved against the control pressure, in the direction of the closed position when a pressure chamber pressure rises in the pressure chamber.

20. A process in accordance with claim 19, wherein the device further comprises:
a control device configured to automatically control and/or regulate flow including to determine the control pressure for moving the closing element in the direction of the open position and to provide the control pressure relative to the chamber pressure in the pressure chamber, so that the movement of the closing element depends on a ratio of the control pressure and the chamber pressure;
an auxiliary pressure chamber with a ventilation opening for passing on breathing gas from the pressure chamber to the patient, wherein the auxiliary pressure chamber is connected to the pressure chamber via a diaphragm opening in a fluid-communicating manner; and
a sensor array configured to detect an actual pressure difference prevailing between the auxiliary pressure chamber and the pressure chamber, wherein the control device is configured to determine a deviation of a desired pressure difference between the auxiliary pressure chamber and the pressure chamber and the detected actual pressure difference to determine the control pressure as a function of the deviation.

21. A device comprising:
an inhalation valve for a ventilation system, the inhalation valve comprising:
an inhalation opening for a flow of breathing gas into a pressure chamber to provide the breathing gas in the pressure chamber for the ventilation of a patient;
a closing element arranged movably, to close the inhalation opening to breathing gas flow in a closed position and to release breathing gas flow, at least partially, in an open position; and
a transmission device connected to the closing element via a connection element, to hold the closing element in the closed position in a starting position of the transmission device;
a control pressure source providing a control pressure in a control pressure chamber cooperating with the transmission device to move the transmission device by the control pressure out of the starting position, wherein the transmission device is configured for a force-transmitting coupling of the pressure chamber with the closing element, so that the closing element, in a position other than the closed position, is moved in the direction of the closed position during a rise in a chamber pressure in the pressure chamber;
a control device configured to automatically control and/or regulate flow including to determine the control pressure for moving the closing element in the direction of the open position and to provide the control pressure relative to the chamber pressure in the pressure chamber, so that the movement of the closing element depends on a ratio of the control pressure and the chamber pressure,
an auxiliary pressure chamber with a ventilation opening for passing on breathing gas from the pressure chamber to the patient, wherein the auxiliary pressure chamber is connected to the pressure chamber via a diaphragm opening in a fluid-communicating manner; and a sensor array configured to detect an actual pressure difference prevailing between the auxiliary pressure chamber and the pressure chamber, wherein the control device is configured to determine a deviation of a desired pressure difference between the auxiliary pressure chamber and the pressure chamber and the detected actual pressure difference to determine the control pressure as a function of the deviation.

\* \* \* \* \*